United States Patent
Morimoto (10) Patent No.: US 9,530,204 B2
(45) Date of Patent: Dec. 27, 2016

(54) METHOD OF PREPARING BIOLOGICAL SPECIMEN

(71) Applicant: OLYMPUS CORPORATION, Tokyo (JP)

(72) Inventor: Nobuhiko Morimoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 727 days.

(21) Appl. No.: 13/894,661

(22) Filed: May 15, 2013

(65) Prior Publication Data

US 2013/0250090 A1     Sep. 26, 2013

Related U.S. Application Data (63) Continuation of application No. PCT/JP2011/067471, filed on Jul. 29, 2011.

(30) Foreign Application Priority Data

Nov. 19, 2010   (JP) ................................. 2010-259094

(51) Int. Cl.
*H04N 7/18*   (2006.01)
*G06T 7/00*   (2006.01)
(Continued)

(52) U.S. Cl.
CPC ............... *G06T 7/0012* (2013.01); *G01N 1/30* (2013.01); *G01N 1/06* (2013.01); *G01N 2001/2873* (2013.01); *H04N 7/18* (2013.01)

(58) Field of Classification Search
CPC ..................... G01N 33/56966; G01N 33/5091; G01N 1/30; G01N 1/31; G01N 1/312; Y01T 436/25; H04N 7/18
(Continued)

(56) References Cited

U.S. PATENT DOCUMENTS 3,448,510 A * 6/1969 Johnson, Jr. .......... B29C 43/361
                                                      206/69
3,932,220 A    1/1976 Liotta
(Continued)

FOREIGN PATENT DOCUMENTS

EP     2 579 019 A1    4/2013
JP     48-13260 A      4/1973
(Continued)

OTHER PUBLICATIONS

International Search Report of related International Application No. PCT/JP2012/080106, mailing date of Jan. 29, 2013.
(Continued)

*Primary Examiner* — Michael Lee
(74) *Attorney, Agent, or Firm* — Westeman, Hattori, Daniels & Adrian, LLP (57) ABSTRACT

A sufficient amount of biological molecules are collected from a desired region in a tissue section with a single operation. Provided is a method of preparing a biological specimen including a sectioning step of sectioning biological tissue along a single cutting plane; a staining step of staining a first tissue section of two tissue sections that have been sectioned in the sectioning step; a stained-image capturing step of acquiring a stained image of the stained tissue section; a non-stained-image capturing step of acquiring a non-stained image in which, with respect to a second tissue section that has been sectioned in the sectioning step, division lines that divide the tissue section into a plurality of segments are defined; and associating steps of associating the non-stained image and the stained image with each other.

9 Claims, 6 Drawing Sheets

(51) Int. Cl.
  *G01N 1/30* (2006.01)
  *G01N 1/06* (2006.01)
  *G01N 1/28* (2006.01)

(58) Field of Classification Search
  USPC .......................................................... 348/79
  See application file for complete search history.

(56) References Cited

U.S. PATENT DOCUMENTS

| | | | |
|---|---|---|---|
| 4,647,543 A | | 3/1987 | Stocker |
| 4,752,347 A | * | 6/1988 | Rada ..................... G01N 1/36 156/382 |
| 4,914,022 A | * | 4/1990 | Furmanski ............. G01N 1/36 435/40.52 |
| 5,998,129 A | | 12/1999 | Schutze et al. |
| 2002/0142412 A1 | | 10/2002 | Ogawa et al. |
| 2002/0192702 A1 | | 12/2002 | Kononen et al. |
| 2002/0197770 A1 | | 12/2002 | Irie |
| 2003/0032082 A1 | | 2/2003 | Leclerc |
| 2003/0184730 A1 | * | 10/2003 | Price .................. G01N 21/6458 356/39 |
| 2004/0014204 A1 | * | 1/2004 | Sheldon ................ A61L 2/238 435/303.1 |
| 2004/0014205 A1 | | 1/2004 | Banes |
| 2006/0121596 A1 | | 6/2006 | Chaumat |
| 2007/0091425 A1 | | 4/2007 | Kawano |
| 2010/0050838 A1 | | 3/2010 | Noguchi et al. |
| 2010/0128988 A1 | * | 5/2010 | Kincaid ............... G06K 9/6253 382/199 |

FOREIGN PATENT DOCUMENTS

| | | |
|---|---|---|
| JP | 55-86173 A | 6/1980 |
| JP | S59-210364 A | 11/1984 |
| JP | 04-197253 A | 7/1992 |
| JP | 06-308118 A | 11/1994 |
| JP | 08-114753 A | 5/1996 |
| JP | 10-229097 A | 8/1998 |
| JP | 11-148887 A | 6/1999 |
| JP | 11-163006 A | 6/1999 |
| JP | 2000-504824 A | 4/2000 |
| JP | 2002-505431 A | 2/2002 |
| JP | 2002-505432 A | 2/2002 |
| JP | 2002-202229 A | 7/2002 |
| JP | 2002-286592 A | 10/2002 |
| JP | 2003-7652 A | 1/2003 |
| JP | 2003-152056 A | 5/2003 |
| JP | 2003-521685 A | 7/2003 |
| JP | 2004-537712 A | 12/2004 |
| JP | 2005-34058 A | 2/2005 |
| JP | 2006-158394 A | 6/2006 |
| JP | 2007-114542 A | 5/2007 |
| JP | 2008-286528 A | 11/2008 |
| JP | 2009-44123 A | 2/2009 |
| JP | 2009-260226 A | 11/2009 |
| JP | 2010-74135 A | 4/2010 |
| JP | 2010-085219 A | 4/2010 |
| WO | 02/37944 A2 | 5/2002 |
| WO | 2008/053916 A1 | 5/2008 |

OTHER PUBLICATIONS

International Search Report of related International Application No. PCT/JP2011/062069, mailing date of Jun. 21, 2011.
Office Actions of Jul. 14, 2014, Oct. 17, 2013, May 17, 2013 of co-pending U.S. Appl. No. 13/686,296.
"Laser microdissection Leica LMD7000", http://www.leica-microsystems.com/jp/products/light-microscopes/life-science-research/laser-microdissection/details/product/leica-lmd7000/, obtained by online-search conducted on Oct. 5, 2010, Cited in Specification, With English translation.
International Search Report for PCT/JP2011/067471, mailing date of Aug. 23, 2011; With English translation.

\* cited by examiner

METHOD OF PREPARING BIOLOGICAL SPECIMEN

CROSS-REFERENCE TO RELATED APPLICATIONS

This is a continuation of International Application PCT/JP2011/067471, with an international filing date of Jul. 29, 2011, which is hereby incorporated by reference herein in its entirety. This application claims the benefit of Japanese Patent Application No. 2010-259094, the content of which is incorporated herein by reference.

TECHNICAL FIELD

The present invention relates to a method of preparing a biological specimen.

Background Art

In the related art, there is a known technique for collecting a segment from a specific region of a tissue section of a biological tissue by means of high-power laser irradiation (for example, see Non Patent Literature 1). The collected segment is used for analyzing biological molecules, such as nucleic acids, proteins, and so forth, existing in a specific region, such as a diseased portion and so forth. At this time, the position of a segment to be collected is accurately determined by staining the tissue section with a dye so that the tissue morphology can be recognized with a microscope.

CITATION LIST

Non Patent Literature

{NPL 1} Leica MICROSYSTEMS, "Laser Microdissection Leica LMD7000" [online] [searched on Oct. 5, 2010], Internet address: URL: http://www.leica-microsystems.com/jp/products/light-microscopes/life-science-research/laser-microdissection/details/product/leica-lmd7000/

SUMMARY OF INVENTION

Technical Problem

In order to recognize details of the tissue morphology in a stained image of a tissue section, the thickness of the tissue section needs to be reduced to several to ten micrometers. Therefore, the amount of biological molecules contained in a single collected segment is low and, in order to collect a sufficient amount of biological molecules for analysis, the collection of segments must be repeated many times by using numerous tissue sections. On the other hand, it is possible to increase the amount of biological molecules that can be obtained from a single segment by increasing the thickness of the tissue section. However, because cells and tissue are overlaid in the thickness direction in that case, the entire tissue section is stained substantially evenly. Therefore, it becomes impossible to accurately determine the position of a segment to be collected from the stained image.

An object of the present invention is to provide a method of preparing a biological specimen with which a sufficient amount of biological molecules can be collected from a desired region of a tissue section with a single operation.

Solution to Problem

The present invention provides a method of preparing a biological specimen including a sectioning step of sectioning biological tissue along a single cutting plane; a staining step of staining a first tissue section of two sections that have been sectioned in the sectioning step; a stained-image capturing step of acquiring a stained image of the tissue section stained in the staining step; a non-stained-image capturing step of acquiring a non-stained image in which, with respect to a second tissue section of the two tissue sections that have been sectioned in the sectioning step, division lines that divide the tissue section into a plurality of segments are defined; and an associating step of associating the non-stained image acquired in the non-stained-image capturing step and the stained image acquired in the stained-image capturing step with each other.

DESCRIPTION OF EMBODIMENT

A method of preparing a biological specimen according to an embodiment of the present invention will be described below with reference to the drawings.

Figure 1:
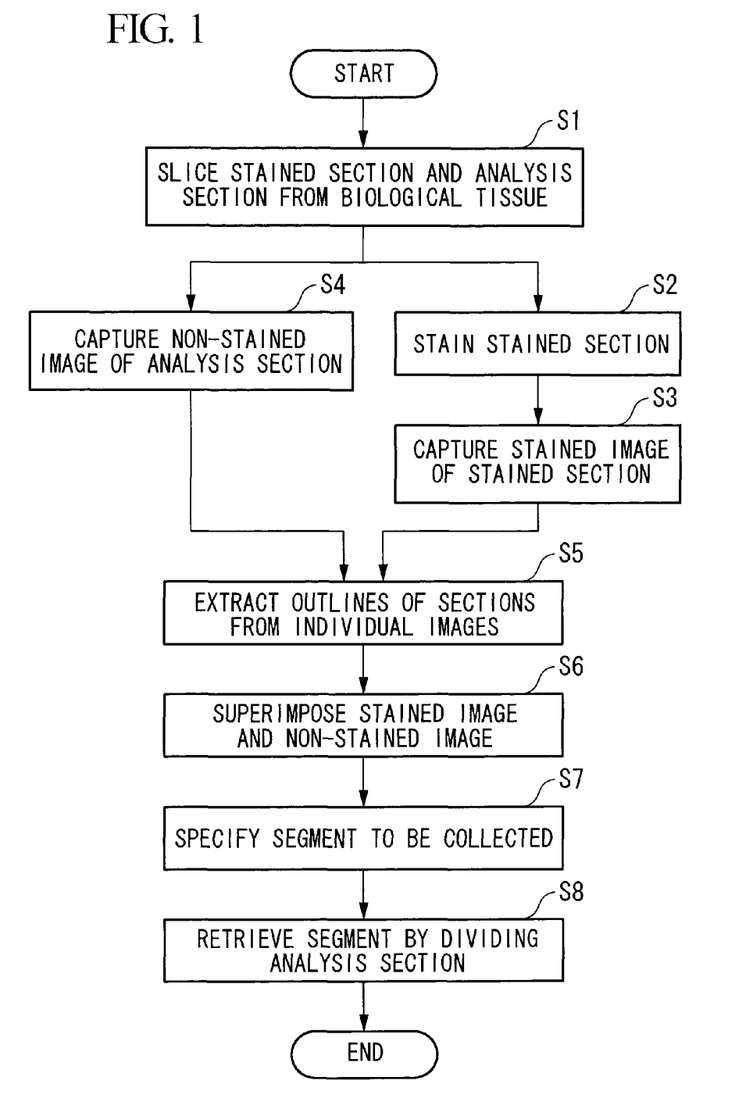
FIG. 1 is a flowchart showing the procedure of a method of preparing a biological specimen according to an embodiment of the present invention.

As shown in FIG. 1, the method of preparing a biological specimen according to this embodiment includes a sectioning step S1 of cutting out two tissue sections 1 and 2 from biological tissue, a staining step S2 of staining the first tissue section 1, a stained-image capturing step S3 of capturing an image of the first tissue section 1 that has been stained, a non-stained-image capturing step S4 of capturing an image of the second tissue section 2 in a state in which it is attached on a substrate 4 having division lines 3, an outline extracting step (associating step) S5 of extracting outlines 7 and 8 of the tissue sections 1 and 2 from acquired stained image 5 and non-stained image 6, respectively, a superimposing step (associating step) S6 of superimposing the stained image 5 and the non-stained image 6, a specifying step S7 of specifying a position to be collected from the tissue section 2 based on the superimposed images, and a retrieving step S8 of retrieving the specified position from the second tissue section 2.

In the sectioning step S1, the two tissue sections 1 and 2 that are cut along a single cutting plane are created. Specifically, the two tissue sections 1 and 2 include cross sections having common tissue morphology. The first tissue section (hereinafter, referred to as a stained section) 1 is sectioned to a thickness of about 1 to 10 μm, that is, an appropriate thickness for stained-image observation. The second tissue section (hereinafter, referred to as an analysis section) 2 is sectioned so as to have a greater thickness than the stained section 1, for example, a thickness of about 50 to 100 μm.

The stained section 1 is stained in the staining step S2. In addition to staining by a dye, staining also refers to processing for visualizing biological molecules under various types of microscopes, such as processing that causes the biological molecules to emit light by means of reactions with enzymes, and so forth, and the method thereof can appropriately be determined in accordance with the biological molecules to be analyzed.

In the stained-image capturing step S3, the stained image 5 is acquired by magnifying the stained section 1 that has been stained in the staining step S2 with a microscope and capturing the image thereof. Any substrate 4 can be used so long as it has a flat surface on which the stained section 1 can be attached. Preferably, a substrate 4 formed of a material that is transparent to visible light, such as glass or the like, is employed so that a transmitted-light image can be observed with a microscope. A substrate 4 that is formed of a material that is semi-transparent or non-transparent to visible light, such as plastic, metal, or the like, may be employed.

Figure 2A:
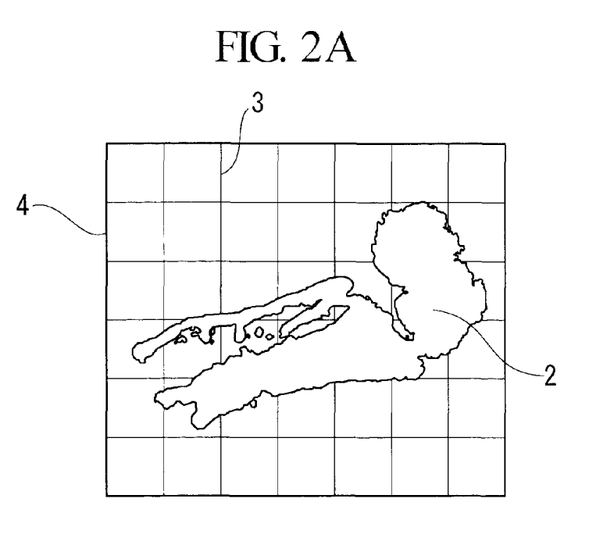
FIG. 2A is a diagram for explaining a non-stained-image capturing step, showing an analysis section before division thereof.

In the non-stained-image capturing step S4, an image of the analysis section 2 is magnified and captured with, for example, a bright-field microscope. As shown in FIG. 2A, the acquired non-stained image 6 shows the analysis section 2 together with the division lines 3 formed on the substrate 4. By doing so, the non-stained image 6 in which the positions of the division lines 3 are defined with respect to the analysis section 2 can be acquired in a simple manner.

Figure 2B:
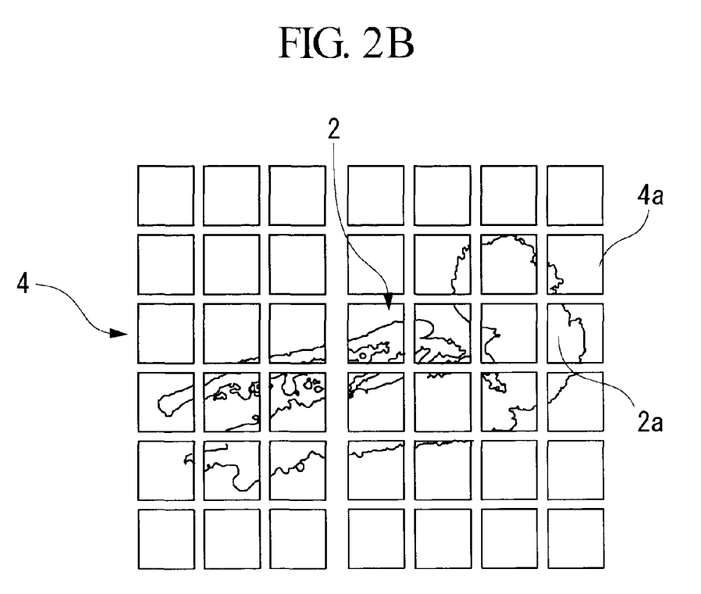
FIG. 2B is a diagram for explaining the non-stained-image capturing step, showing the analysis section after division thereof.

The division lines 3 are formed so that an operator can divide the substrate 4 at the positions thereof: for example, they are grooves formed on the substrate 4. The grooves can be formed by laser processing, chemical etching, dicing, or manually by the operator using a glass cutter or the like. By doing so, as shown in FIG. 2B, the substrate 4 can be divided into a plurality of small pieces 4a at the positions of the division lines 3 by the operator pulling the substrate 4 in the surface direction. At this time, the analysis section 2 attached on the substrate 4 can also be divided, together with the substrate 4, into a plurality of segments 2a along the division lines 3. The spacing between the division lines 3 can appropriately be changed in accordance with the sizes of the segments 2a to be collected from the analysis section 2. It is preferable that the spacing between the division lines 3 be from 0.05 to 5.0 mm so that a sufficient amount of biological molecules are contained in the collected segments 2a, while still enabling collection of the segments 2a in a desired region in the analysis section 2 with a sufficiently fine positional precision.

Although the method of pulling the substrate 4 is not particularly limited, the substrate 4 can be divided in a simple manner by, for example, attaching the substrate 4 on an adhesive sheet that can be extended in a direction parallel to the surface thereof and by pulling the adhesive sheet in the direction parallel to the surface thereof.

The division lines 3 may be formed of, for example, gaps between the plurality of small pieces 4a that are divided in advance and regularly arranged on the adhesive sheet. By doing so, the substrate 4 can be divided more reliably when the operator pulls the substrate 4 in the surface direction.

Figure 3:
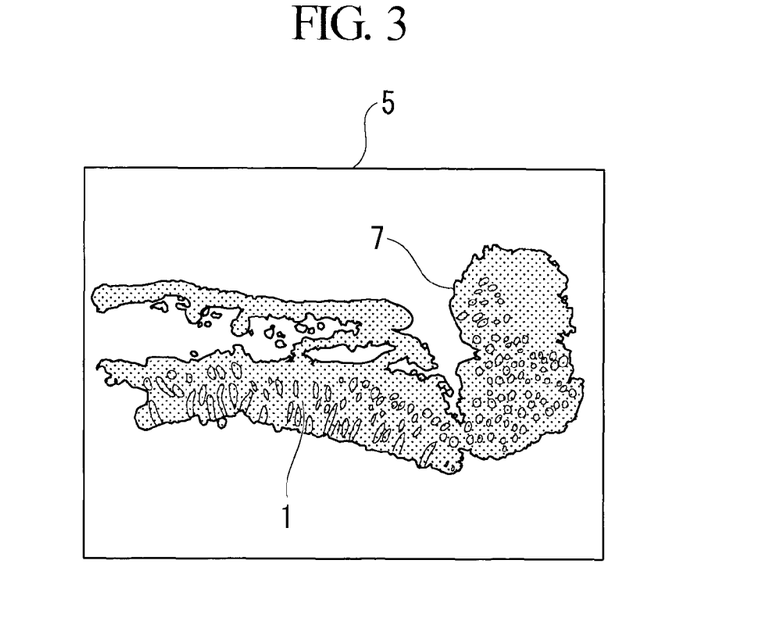
FIG. 3 is a diagram showing a stained image in which the outline of a stained section is extracted.
Figure 4:
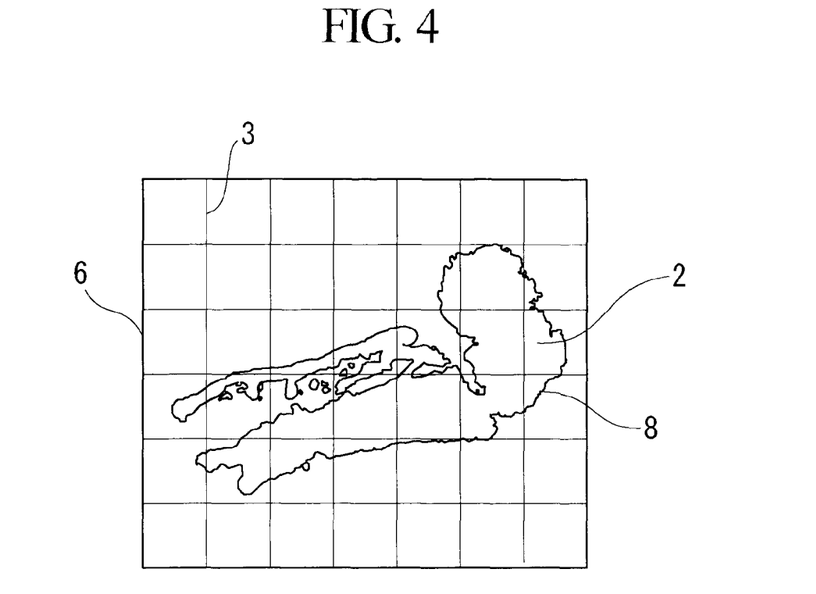
FIG. 4 is a diagram showing a non-stained image in which the outline and division lines of the analysis section are extracted.

In the outline extracting step S5, the outline 7 of the stained section 1 is extracted from the stained image 5, as shown in FIG. 3, and the outline 8 of the analysis section 2 and the division lines 3 are extracted from the non-stained image 6, as shown in FIG. 4. A known method, for example, a method in which the differences in brightness of adjacent pixels or derivatives thereof are utilized, can be employed as the method of extracting the outlines 7 and 8 and the division lines 3. An appropriate image processing may be applied so that the outlines 7 and 8 are more clearly extracted. The image processing includes, for example, gamma curve correction, brightness-darkness adjustment, contrast enhancement, binarization of luminance, brightness inversion, noise removal by means of a median filter or the like, and so on.

Figure 5:
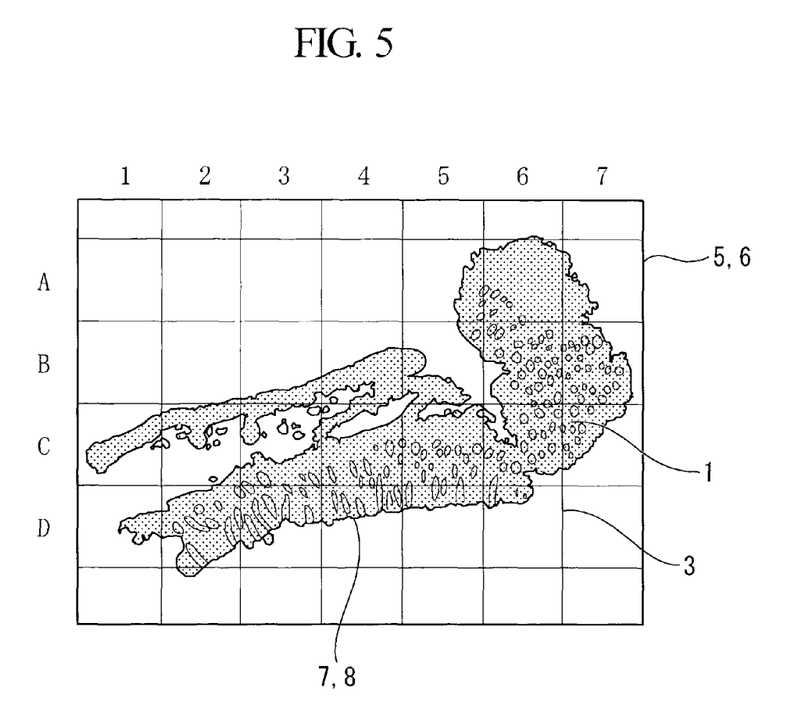
FIG. 5 is a diagram showing a state in which the stained image and the non-stained image are displayed in a superimposed manner.

In the superimposing step S6, the stained image 5 and the non-stained image 6 are displayed in a superimposed manner so that the positions of the two extracted outlines 7 and 8 are matched, as shown in FIG. 5. To match the two outlines 7 and 8, for example, the two images 5 and 6 should be superimposed at a relative position where the cross-correlation value of the outlines 7 and 8 becomes the largest. By doing so, individual positions are associated with each other between the stained section 1 and the analysis section 2, and, in the displayed superimposed images, the division lines 3 are also defined with the same positional relationship with respect to the stained section 1 as that defined with respect to the analysis section 2.

Here, the individual sections 1 and 2 in the stained image 5 and the non-stained image 6 sometimes differ in orientation and front-and-back direction, and also differ in magnification as a result of being captured with different microscopes and cameras. Therefore, the images 5 and 6 may be appropriately manipulated by applying rotation, reversal, shrinking, enlarging, or the like to one of the images so that the extracted outlines 7 and 8 are more accurately matched.

In the specifying step S7, the operator determines a region to be collected by observing, in the displayed superimposed images, the tissue morphology in the stained image 5, and specifies segments 2a located at positions that match with the determined region. For example, row numbers A, B, C, and D, and column numbers 1, 2, 3, and so on are added to the segments 2a that are segmented by the division lines 3, and the positions of segments 2a to be collected are specified by using combinations of the row number and column number.

In the retrieving step S8, the substrate 4 and the analysis section 2 are divided along the division lines 3, and the segments 2a at positions specified by the operator in the specifying step S7 are selected and retrieved. By doing so, the segments 2a that have the same tissue morphology as the region determined based on the stained image 5 can be collected from the analysis section 2 in a state in which they are attached on the small pieces 4a of the substrate 4. From the retrieved segments 2a, biological molecules, for example, nucleic acids, proteins, polysaccharides, lipids, and so forth, can be analyzed.

In this case, with this embodiment, the segments 2a collected from the analysis section 2, which is thicker than the thinner stained section 1, contain a sufficient amount of biological molecules. Therefore, an advantage is afforded in that a task that conventionally requires collection of segments to be repeated many times by using numerous stained sections to collect a sufficient amount of biological molecules for analysis can be completed by performing the task just once or a few times.

In addition, in the case of such a thick analysis section 2, because cells and tissue are overlaid in the thickness direction, the entirety thereof is substantially evenly stained during staining, thus making it difficult to recognize the tissue morphology under a microscope. Thus, the thin stained section 1 having the same tissue morphology as the analysis section 2 is created, and, by associating the stained image 5 of the stained section 1 and the non-stained image 6 of the analysis section 2, it is possible to ascertain the tissue morphology in detail at individual positions in the analysis section 2 by referring to the stained section 1. Accordingly, an advantage is afforded in that the segments 2a can be collected from a desired site even from the analysis section 2.

In addition, as a method of associating positions of the stained section 1 and the analysis section 2, it is conceivable to employ a method in which markers are added to individual corresponding positions in the tissue sections 1 and 2. In the case of this method, the markers need to be added with high positional precision by comparing the two tissue sections 1 and 2 in detail to determine the positions where the markers are added. Therefore, there is a problem in that the number of processes is increased in addition to the operation becoming complicated. In contrast, with this embodiment, because it is necessary just to capture the two tissue sections 1 and 2 and display these images in a superimposed manner, an advantage is afforded in that the two tissue sections 1 and 2 can be associated with each other with a simple task.

Figure 6:
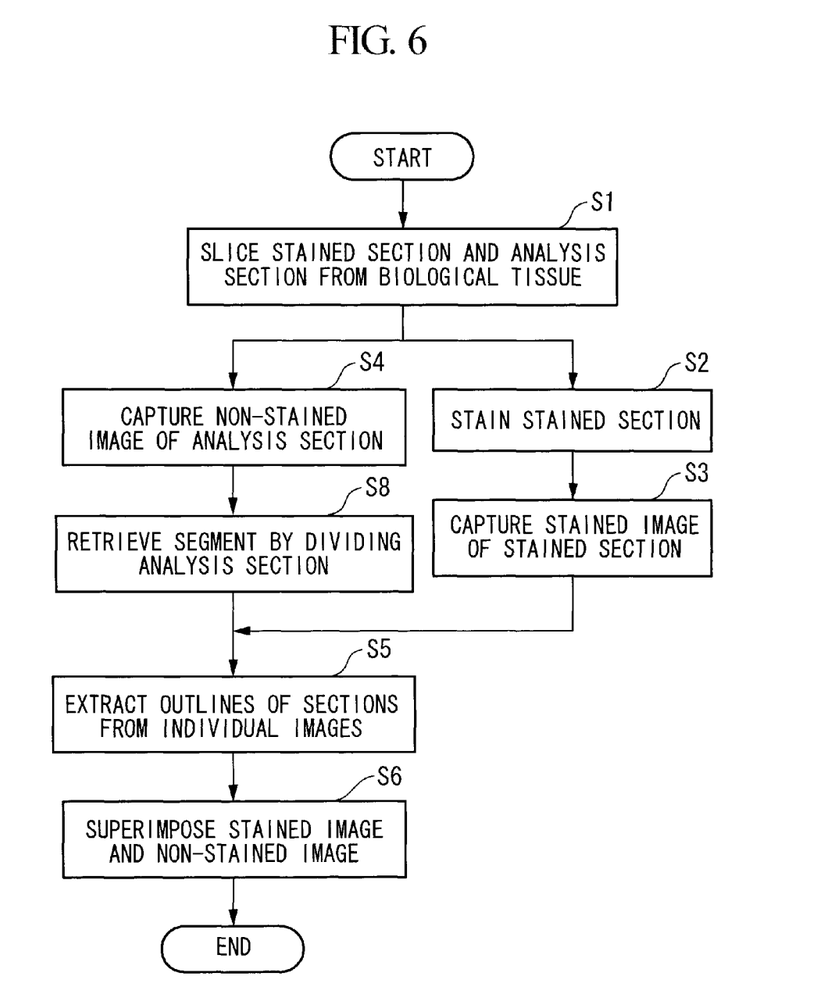
FIG. 6 is a flowchart showing a modification of the method of preparing a biological specimen according to this embodiment.

Note that, in this embodiment, the desired segments 2a are selectively retrieved by dividing the analysis section 2 after associating the positions of the segments 2a in the analysis section 2 and the positions in the stained section 1 with each other; however, alternatively, the positions of the individual segments 2a and the positions in the stained section 1 may be associated with each other by capturing the stained image 5 after dividing the analysis section 2 and retrieving all segments 2a, as shown in FIG. 6.

Figure 7:
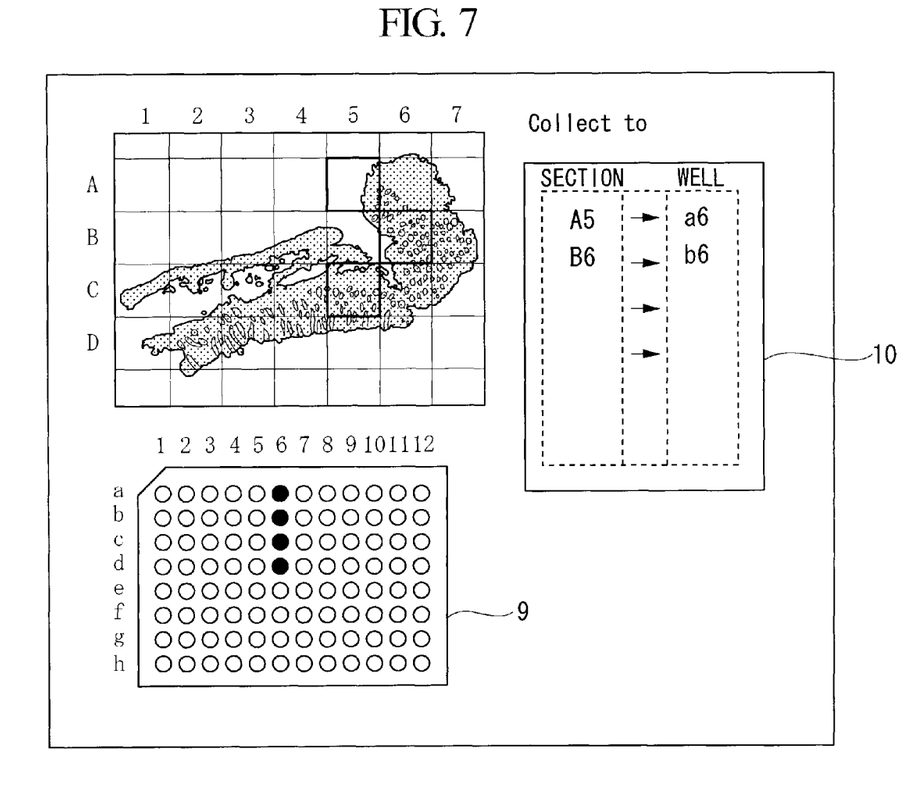
FIG. 7 is a diagram for explaining an example method of adding positional information to individual segments in the method of preparing a biological specimen shown in FIG. 6.

In this case, the individual segments 2a are retrieved by adding positional information in the analysis section 2. For example, as shown in FIG. 7, when retrieving the segments 2a into a multi-well plate 9, the row numbers and column numbers serving as the positional information for the individual segments 2a are recorded in a list 10 in association with well positions in the multi-well plate 9 into which they are retrieved. By doing so, it is possible to ascertain which segments 2a are accommodated in which cells even after they are retrieved.

By doing so, after analyzing biological molecules contained in the individual segments 2a by prioritizing the processing in which the analysis section 2 is used, it is possible to ascertain what kind of tissue morphology possessed by the segments 2a that have given the individual analysis results by searching and referring to a site in the stained section 1 corresponding to the individual segments 2a based on the positional information of the individual segments 2a. Accordingly, because the time required between creation of the analysis section 2 and analysis of biological molecules is reduced, for example, even for easily degenerated biological molecules like mRNA, analysis can be performed quickly while they are fresh, making it possible to obtain accurate analysis results.

In addition, in this embodiment, the outlines 7 and 8 of the tissue sections 1 and 2 are extracted from the individual images 5 and 6 in order to superimpose the stained image 5 and the non-stained image 6; however, alternatively, a plurality of identical feature points may be extracted from the individual images 5 and 6, and these images 5 and 6 may be superimposed so that positions of the extracted feature points are matched. By doing so, it is also possible to superimpose the images 5 and 6 so that the two tissue sections 1 and 2 exactly overlap.

The feature points that can be used include, for example, sharply pointed portions in the tissue sections 1 and 2, luminal structures therein, and so forth. The feature points are extracted by, for example, a user inputting them into the individual images 5 and 6. The number of feature points specified at this time may be any number equal to or greater than two; however, in order to enhance the positional precision when superimposing, three or more are preferable.

In addition, four or more feature points may be extracted and three of the four or more feature points may be used, cross-correlation between the two images 5 and 6 when the three feature points used are matched may be calculated, and a combination of the feature points for which cross-correlation is the greatest may be used in the end. By doing so, it is possible to superimpose the two images 5 and 6 so that the two tissue sections 1 and 2 are matched more accurately, for example, even if, of the feature points specified by the user, there are some feature points whose positions do not match between the two images 5 and 6.

In addition, with this embodiment, the division lines 3 for dividing the analysis section 2 are defined with respect to the analysis section 2 by attaching the analysis section 2 on the substrate 4 on which the division lines 3 are formed; however, alternatively, the division lines may be defined in the non-stained image 6 that is captured after capturing the image of the analysis section 2, and the analysis section 2 may be divided in accordance with these defined division lines. The division lines may be defined by the operator by inputting them into the non-stained image 6 or they may be defined by means of image processing.

In addition, with this embodiment, the segments 2a to be collected are specified in the state in which the stained image 5 and the non-stained image 6 are superimposed; however, alternatively, the segments 2a to be collected may be specified by separately displaying the stained image 5 and the non-stained image 6 side-by-side and by comparing the two images 5 and 6. In this case, positions to be collected are identified first by observing the stained image 5 (identifying step), the tissue sections 1 and 2 in the two images 5 and 6 are visually compared, and the segments 2a at positions corresponding to the identified positions are determined (determining step). By doing so, it is also possible to specify and collect the segments 2a from the analysis section 2 in a region having desired tissue morphology.

In addition, with this embodiment, the non-stained image 6 is captured before dividing the analysis section 2; however, alternatively, the non-stained image 6 of the individual segments 2a may be captured after the division, and the analysis section 2 may be reconstructed into the state before the division thereof by connecting the individual segments 2a at the positions of the division lines 3 by means of image processing. By doing so, it is also possible to associate the positions of the analysis section 2 and the stained section 1 with each other as in the embodiment described above.

REFERENCE SIGNS LIST

1 stained section
2 analysis section
2a segment
3 division line
4 substrate
4a small piece
5 stained image
6 non-stained image 7, 8 outline
9 multi-well plate
10 list
S1 sectioning step
S2 staining step
S3 stained-image capturing step
S4 non-stained-image capturing step
S5 outline extracting step (associating step)
S6 superimposing step (associating step)
S7 specifying step
S8 retrieving step

The invention claimed is:

1. A method of preparing a biological specimen comprising:
   a sectioning step of sectioning biological tissue along a single cutting plane;
   a staining step of staining a first tissue section of two tissue sections that have been sectioned in the sectioning step;
   a stained-image capturing step of acquiring a stained image of the tissue section stained in the staining step;
   a non-stained-image capturing step of acquiring a non-stained image in which, with respect to a second tissue section of the two tissue sections that have been sectioned in the sectioning step, division lines that divide the second tissue section into a plurality of segments are defined;
   an associating step of associating the non-stained image acquired in the non-stained-image capturing step and the stained image acquired in the stained-image capturing step with each other;
   a specifying step of specifying the segments to be collected from the tissue section; and
   a retrieving step of dividing the tissue section into the plurality of segments along the division lines and retrieving the segments that have been specified in the specifying step.

2. The method of preparing a biological specimen according to claim 1,
   wherein, in the non-stained-image capturing step, the second tissue section is placed on a substrate that can be divided along the division lines, and an image thereof is captured.

3. The method of preparing a biological specimen according to claim 1,
   wherein the associating step includes an outline extracting step of individually extracting outlines of the two tissue sections from the non-stained image and the stained image; and a superimposing step of superimposing the non-stained image and the stained image so that the two outlines extracted in the outline extracting step are matched.

4. The method of preparing a biological specimen according to claim 1,
   wherein the associating step includes a feature point extracting step of extracting a plurality of identical feature points from the non-stained image and the stained image; and a superimposing step of superimposing the non-stained image and the stained image so that positions of the feature points extracted in the feature point extracting step are matched.

5. The method of preparing a biological specimen according to claim 1,
   wherein the specifying step includes an identifying step of identifying a position to be collected from the tissue section based on the stained image; and a determining step of determining, based on the non-stained image, the segments associated with the position to be collected that has been identified in the identifying step.

6. A method of preparing a biological specimen comprising:
   a sectioning step of sectioning biological tissue along a single cutting plane;
   a staining step of staining a first tissue section of two tissue sections that have been sectioned in the sectioning step;
   a stained-image capturing step of acquiring a stained image of the tissue section stained in the staining step;
   a non-stained-image capturing step of acquiring a non-stained image in which, with respect to a second tissue section of the two tissue sections that have been sectioned in the sectioning step, division lines that divide the second tissue section into a plurality of segments are defined;
   an associating step of associating the non-stained image acquired in the non-stained-image capturing step and the stained image acquired in the stained-image capturing step with each other; and
   a retrieving step of dividing the tissue section into the plurality of segments along the division lines and retrieving the individual segments by adding positional information in the tissue section.

7. The method of preparing a biological specimen according to claim 6,
   wherein, in the non-stained-image capturing step, the second tissue section is placed on a substrate that can be divided along the division lines, and an image thereof is captured.

8. The method of preparing a biological specimen according to claim 6,
   wherein the associating step includes an outline extracting step of individually extracting outlines of the two tissue sections from the non-stained image and the stained image; and a superimposing step of superimposing the non-stained image and the stained image so that the two outlines extracted in the outline extracting step are matched.

9. The method of preparing a biological specimen according to claim 6,
   wherein the associating step includes a feature point extracting step of extracting a plurality of identical feature points from the non-stained image and the stained image; and a superimposing step of superimposing the non-stained image and the stained image so that positions of the feature points extracted in the feature point extracting step are matched.

* * * * *